(12) United States Patent
Berk et al.

(10) Patent No.: US 9,011,460 B2
(45) Date of Patent: Apr. 21, 2015

(54) FOREIGN OBJECT EXTRACTOR

(71) Applicants: Joseph Berk, Owings Mill, MD (US); Jon L. Roberts, Great Falls, VA (US)

(72) Inventors: Joseph Berk, Owings Mill, MD (US); Jon L. Roberts, Great Falls, VA (US)

( * ) Notice: Subject to any disclaimer, the term of this patent is extended or adjusted under 35 U.S.C. 154(b) by 0 days.

(21) Appl. No.: 13/718,091

(22) Filed: Dec. 18, 2012

(65) Prior Publication Data

US 2013/0123758 A1 May 16, 2013

Related U.S. Application Data

(63) Continuation-in-part of application No. 12/017,148, filed on Jan. 21, 2008, now abandoned.

(51) Int. Cl.
| | |
|---|---|
| *A61F 11/00* | (2006.01) |
| *A61B 17/50* | (2006.01) |
| *A61B 17/22* | (2006.01) |
| *A61B 17/00* | (2006.01) |
| *A61B 17/30* | (2006.01) |

(52) U.S. Cl.
CPC ........... *A61B 17/50* (2013.01); *A61B 17/22031* (2013.01); *A61B 2017/00544* (2013.01); *A61B 2017/00561* (2013.01); *A61B 2017/22035* (2013.01); *A61B 2017/308* (2013.01)

(58) Field of Classification Search
CPC ............. A61B 17/50; A61B 2017/308; A61B 17/22031; A61B 2017/00561; A61B 2017/22035; A61B 2017/00544; B25B 11/007

USPC .............................................. 606/1, 109, 127
See application file for complete search history.

(56) References Cited

U.S. PATENT DOCUMENTS

| | | | | |
|---|---|---|---|---|
| 2,384,334 | A | * | 9/1945 | Olson .......................... 294/187 |
| 3,387,610 | A | * | 6/1968 | Richmond .................... 604/216 |
| 4,356,989 | A | * | 11/1982 | Ireland ....................... 248/205.9 |
| 5,073,347 | A | * | 12/1991 | Garren et al. ................. 422/501 |
| 5,236,455 | A | * | 8/1993 | Wilk et al. ...................... 623/10 |
| 6,039,629 | A | * | 3/2000 | Mitchell ........................ 450/57 |
| 7,631,579 | B2 | * | 12/2009 | Johnson et al. .............. 81/53.12 |
| 8,555,749 | B2 | * | 10/2013 | Gatski ......................... 81/53.11 |
| 2004/0030319 | A1 | | 2/2004 | Korkor et al. |
| 2006/0020334 | A1 | * | 1/2006 | Lashinski et al. ............ 623/2.11 |
| 2006/0167469 | A1 | * | 7/2006 | Arden ........................... 606/109 |
| 2006/0247572 | A1 | * | 11/2006 | McCartney ..................... 604/19 |
| 2006/0276752 | A1 | * | 12/2006 | Bierman et al. .............. 604/174 |
| 2007/0125202 | A1 | * | 6/2007 | Johnson et al. .............. 81/53.11 |

* cited by examiner

*Primary Examiner* — Tuan V Nguyen
*Assistant Examiner* — Tin Nguyen
(74) *Attorney, Agent, or Firm* — The Marbury Law Group, PLLC

(57) ABSTRACT

The foreign object extractor has an elongated hollow tube with a central lumen through its entire length providing fluid connection between an engaging end and a vacuum source. The engaging end has a nominally round transverse cross-section and is shaped to engage a foreign object to be removed from the human body. The engaging end flares so as to expose the internal surface of the elongated hollow tube for engagement with the foreign object. An adhesive is disposed on the exposed internal flared surface of the distal end. Pneumatic suction is applied through the lumen of the extractor and the suction serves to bring the foreign object into contact with the adhesive coated surface of the extractor to form a bond between the extractor and the object to be extracted.

7 Claims, 6 Drawing Sheets

FOREIGN OBJECT EXTRACTOR

FIELD OF THE INVENTION

Embodiments are directed to the art of medical instruments, and more particularly to instruments for removal of objects from within a living body.

BACKGROUND INFORMATION

Commonly objects become lodged in a living body and need to be removed. Various types and sizes of forceps have been used in the past to seize and extract such embedded objects.

The use of forceps for object extraction can be traumatic to cartilage and soft tissue. Forceps are formed of metal or rigid plastic, which are hard and can cause pain and tearing of tissue even when wielded with the gentlest technique possible.

An endoscopic surgical instrument has been proposed, which relies entirely upon vacuum pressure to maintain a grip on the foreign body. Because embedded foreign bodies can have irregular shapes or surface textures, vacuum pressure alone is sometimes unreliable in maintaining a grip on the object during extraction. If the object has a hole, such as a bead, the vacuum pressure will be unable to grip the object. Also, because some embedded foreign bodies are easily frangible and because control of the amount of vacuum pressure applied is difficult, reliance on vacuum pressure alone for retention of the object during extraction risks fragmenting the object.

SUMMARY OF THE INVENTION

Various embodiments illustrated herein result in a foreign body extractor instrument that is more pliable than metal or rigid plastic and grips objects securely for extraction. Such an extractor can apply extracting force to a foreign object without need to slide past the foreign object.

The foreign object extractor is an elongated hollow tube with a central lumen through its entire length. A distal engaging end is shaped to engage a foreign object and has a nominally round transverse cross-section. In an embodiment, the shape of the engaging end flares so as to allow a wider cross section and surface area of the end of the tube to contact the foreign object for engagement with the foreign object. A fast-curing adhesive is disposed on the exposed flared surface of the distal end. Pneumatic suction is applied through the lumen of the extractor and the suction serves to bring the foreign object into contact with the adhesive coated surface of the extractor to form a substantially permanent and/or non-releasable bond between the distal end and the foreign body to be removed. By "substantially permanent" or "non-releasable bond" applicants are referring to a bond between the foreign object to be removed and the adhesive coated end of the lumen such that the bond is sufficiently strong such that the lumen cannot easily be separated from the foreign object to be removed without damaging the lumen and rendering it unusable or causing destruction or physical damage or deformation to the foreign object being removed. Substantially permanent and/or non-releasable bond may further mean that the bond between the adhesive coated distal end and the foreign object being removed remains in place after the foreign object is removed.

In an embodiment, the foreign object extractor is more pliable than metal.

In another embodiment, the foreign object extractor has the capability to securely grip an object without relying solely on vacuum pressure.

In yet another embodiment, the foreign object extractor has the capability to adhesively grip frangible or hollow articles unsuited to vacuum pressure.

In still another embodiment, the foreign object extractor applies extracting force to a foreign object without the need to slide past the foreign object.

DETAILED DESCRIPTION

In the various descriptions of embodiments that follow, it is anticipated that the adhesives illustrated will be selected from those that will form substantially permanent and/or non-releasable bonds (collectively referred to herein as non-releasable bonds") between the engaging adhesive coated ends of the elongate extractor bodies and the foreign objects to be extracted.

Figure 1:
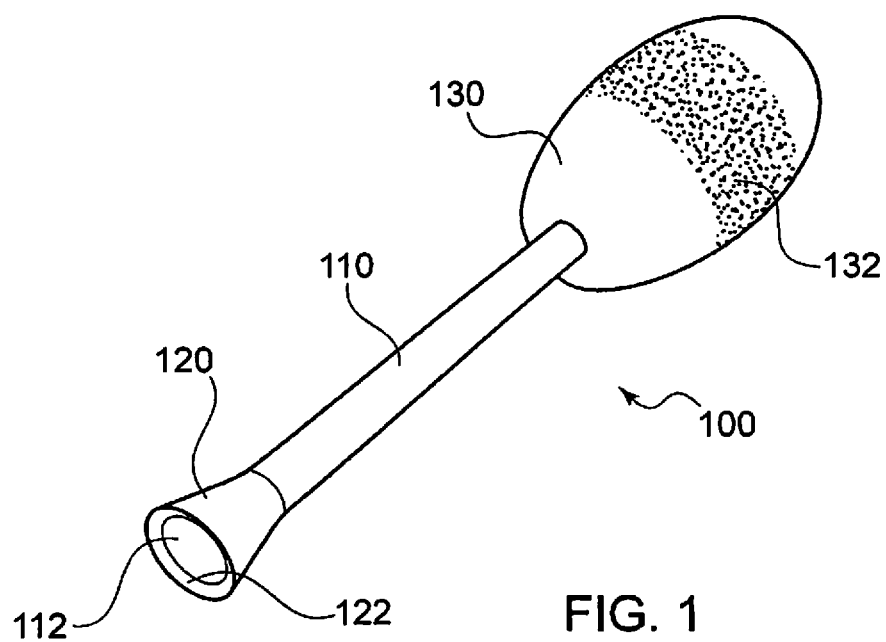
FIG. 1 illustrates a perspective view of a foreign object extractor according to a first embodiment.

Referring to FIG. 1, a perspective view of a foreign object extractor according to a first embodiment is illustrated. The extractor 100 has an elongate body 110 or tube with a flared engaging end 120. The body 110 is hollow with a lumen 112 extending the entire length of the body 110 from the engaging end 120 to a vacuum bulb 130. The tubular body 110 is resiliently flexible. The rim of the engaging end 120 has an adhesive coated annular surface 122. In this illustrated embodiment the periphery of the vacuum bulb 130 has a surface 132 to enhance grip although this is not meant as a limitation.

Although the amount of suction that can be provided at the engaging end 120 is limited by the size of the vacuum bulb 130, this first embodiment extractor 100 has the advantage of being portable so that it is useful away from a sustained vacuum source. Further it is anticipated that this, and the other embodiments illustrated herein are disposable and will be single use only so as to avoid any contamination and transmission of disease or pathogens from one patient to the next.

It should also be noted that in this and other illustrated embodiments, a flared end is illustrated. This is not meant as a limitation since a flared end may not be required for all situations. Yet another embodiment may simply have a tube whose end diameter is the same as the entire tube, but having a fast curing adhesive disposed on the end surface of the lumen that comes in contact with the foreign object. In an embodiment (illustrated below) the fast curing adhesive may be a light curing adhesive. Shining a light of an appropriate wavelength onto the elongate body 110 will lead to the light being conducted down the tube, as in a fiber optic type conduction to the light curing adhesive, thereby creating a bond with the foreign object when the adhesive is cured.

In addition, it is anticipated that flared ends of varying sizes will be represented by alternate embodiments. The flare size would be selected by the practitioner based on the canal or passage in which the foreign object is embedded and by the shape of the embedded foreign body.

Figure 2:
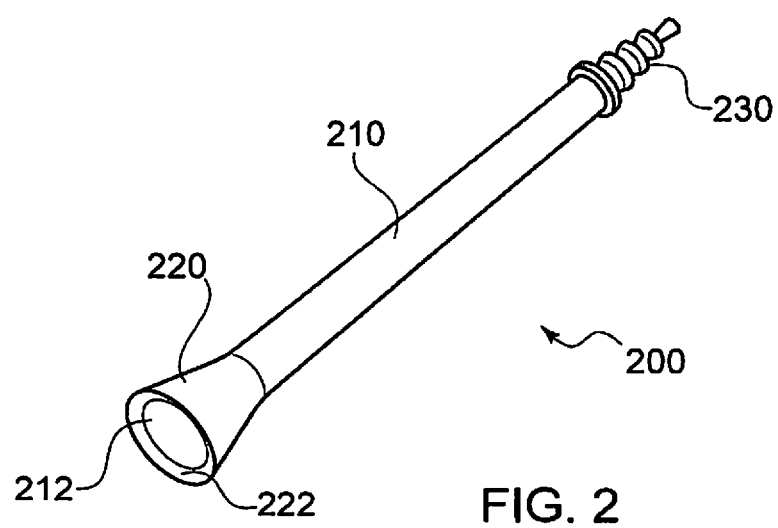
FIG. 2 illustrates a perspective view of a foreign object extractor according to a second embodiment.

Referring to FIG. 2, a perspective view of a foreign object extractor according to a second embodiment is illustrated. The extractor 200 has an elongate body 210 with a flared engaging end 220. The body 210 is hollow with a lumen 212 extending the entire length of the body 210 from the engaging end 220 to a vacuum fitting 230. The tubular body 210 is resiliently flexible. The inside rim of the engaging end 220 has an annular surface 222 on which a fast curing adhesive is disposed.

The vacuum fitting 230 provides for easy connection to a vacuum line of a vacuum pump. This second embodiment extractor 200 provides for application of a continuous vacuum which may be available from a portable vacuum pump or from a vacuum source in a permanent facility such as an operating or emergency room. Such room suction vacuum lines are common infrastructure that may be utilized in a hospital, clinic, urgent care, or trauma center setting.

Figure 3:
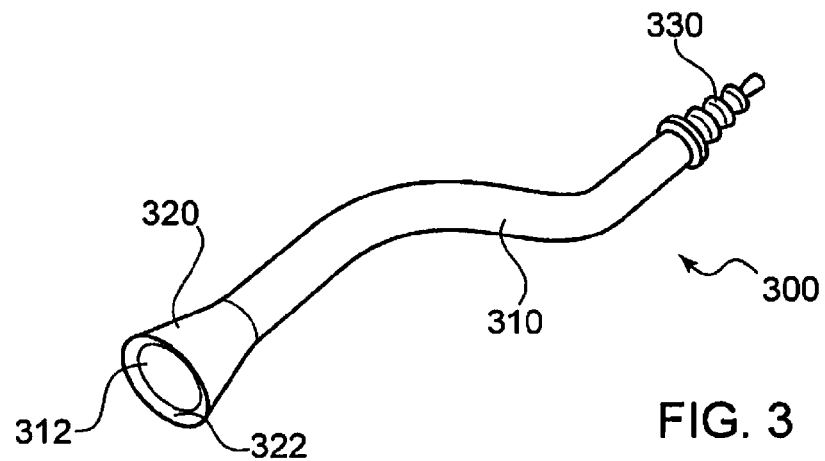
FIG. 3 illustrates a perspective view of a foreign object extractor according to a third embodiment.

Referring to FIG. 3, a perspective view of a foreign object extractor according to a third embodiment is illustrated. The extractor 300 has an elongate body 310 with a flared engaging end 320. The body 310 is hollow with a lumen 312 extending the entire length of the body 310 from the engaging end 320 to a vacuum fitting 330. The tubular body 310 is plastically flexible. The rim of the engaging end 320 has an annular adhesive surface 322 on which a fast curing adhesive is disposed.

Similarly as in the second embodiment, the vacuum fitting 330 provides for easy connection to a vacuum line of a vacuum pump or a permanent vacuum source.

Figure 4:
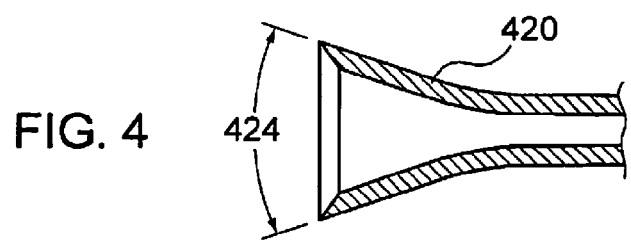
FIG. 4 illustrates a cross section view of a flared engaging end of a foreign object extractor having a moderate flare.

Referring to FIG. 4, a cross section view of a flared engaging end 420 of a foreign object extractor having a moderate flare is illustrated. The flare angle 424 is selected to provide positive engagement of the engaging end 420 with medium sized objects such as those the size of marbles. The illustrated moderate flare angle 424 is approximately 45 degrees, but a moderate flare angle may range from 37 to 53 degrees.

Figure 5:
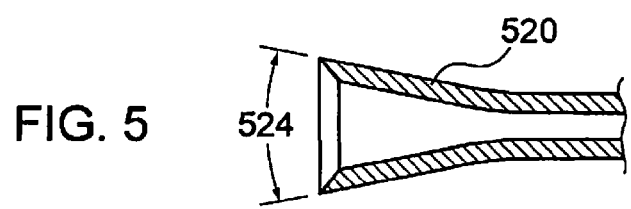
FIG. 5 illustrates a cross section view of a flared engaging end of a foreign object extractor having a narrow flare.

Referring to FIG. 5, a cross section view of a flared engaging end of a foreign object extractor having a narrow flare is illustrated. The flare angle 524 is selected to provide positive engagement of the engaging end 520 with small sized objects such as those the size of Tic-tac® mints. The illustrated narrow flare angle 524 is approximately 30 degrees, but a narrow flare angle may range from 20 to 37 degrees with other flare angles possible as well, again depending on the circumstances.

Figure 6:
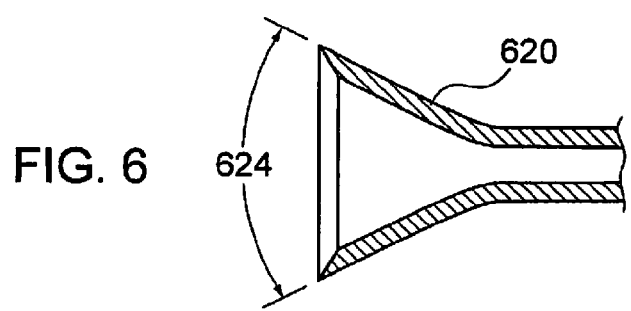
FIG. 6 illustrates a cross section view of a flared engaging end of a foreign object extractor having a wide flare.

Referring to FIG. 6, a cross section view of a flared engaging end of a foreign object extractor having a wide flare is illustrated. The flare angle 624 is selected to provide positive engagement of the engaging end 620 with larger sized objects such as those the size of batteries. The illustrated wide flare angle 624 is approximately 60 degrees, but a wide flare angle may range from 53 to 75 degrees.

Figure 7:
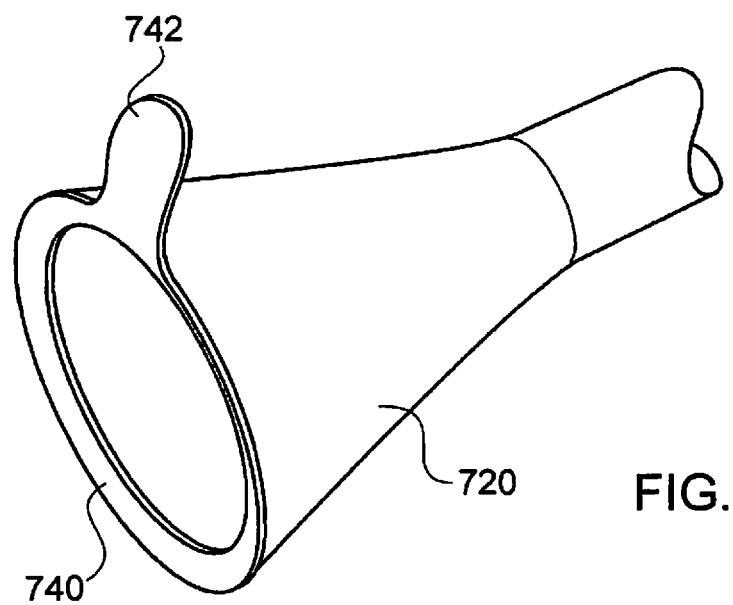
FIG. 7 illustrates a detail view of the flare end of the foreign object extractor.

Referring to FIG. 7, a detail view of the flared engaging end 720 of the foreign object extractor is illustrated. A protective cover 740 is disposed over the inner rim of the engaging end 720 to cover up and protect the adhesive coated surface (not shown in this view; refer to FIGS. 1-3) prior to use. The protective cover 740 has a tab 742 sized to be grasped so that the protective cover 740 can be pulled off to expose the adhesive surface immediately prior to use of the extractor.

In the embodiments illustrated in FIGS. 1-7 and 9, various flare angles are illustrated. This is not meant as a limitation however since the end of the flare or non-flared tube may simply be perpendicular to the axis of the tube and can be equally useful without a flare or flare angle of the end.

Figure 8:
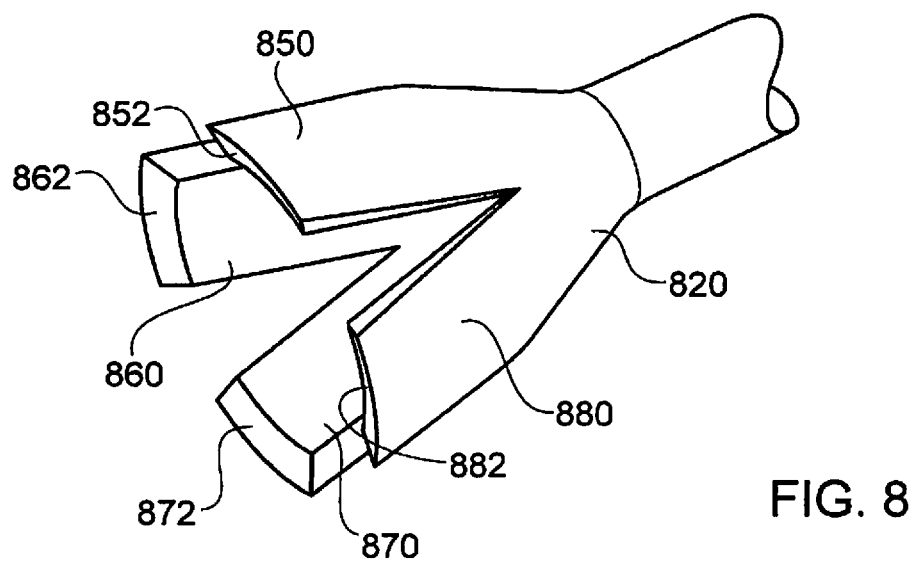
FIG. 8 illustrates a detail view of the flare end of the foreign object extractor having a segmented configuration.

Referring to FIG. 8, a detail view of the engaging end of the foreign object extractor having a segmented configuration is illustrated. The flared engaging end 820 is divided at its extreme periphery into four distinct engaging segments 850, 860, 870, 880 that are resiliently flexible so as to move independently of one another to a degree. The extreme end of each of the engaging segments 850, 860, 870, 880 has a respective adhesive coated surface 852, 862, 872, 882.

While the segmentation of the engaging end 820 will affect the strength of the vacuum force applied to the foreign object, the vacuum force will nevertheless provide some degree of suction force to cause engagement of a foreign body with the adhesive coated surfaces 852, 862, 872, 882 on the ends of the engaging segments 850, 860, 870, 880. The advantage of segmentation of the engaging end 820 is that it increases the likelihood of obtaining a secure engagement with a foreign object that has an unforeseen, irregular shape. In addition, this segmented shape may be used to further engage surfaces of a more regular object (i.e., such as the surface of a marble, etc.) as illustrated above. It will be appreciated by those skilled in the art that the number of engaging segments illustrated is not meant as a limitation. Depending on the specific situation, the age of the patient, the object to be extracted and other factors, the number of segments of the segmented end will vary.

The segmented end illustrated in FIG. 8 may also comprise adhesive coated surfaces on the interior portion of the engaging segments 850, 860, 870, 880. Further, this segmented end may surround a tube which itself has an adhesive coated surface on its end similar to that illustrated in FIG. 2, 222 in order to have further adhesive coated surfaces to engage the foreign object to be extracted.

Figure 8A:
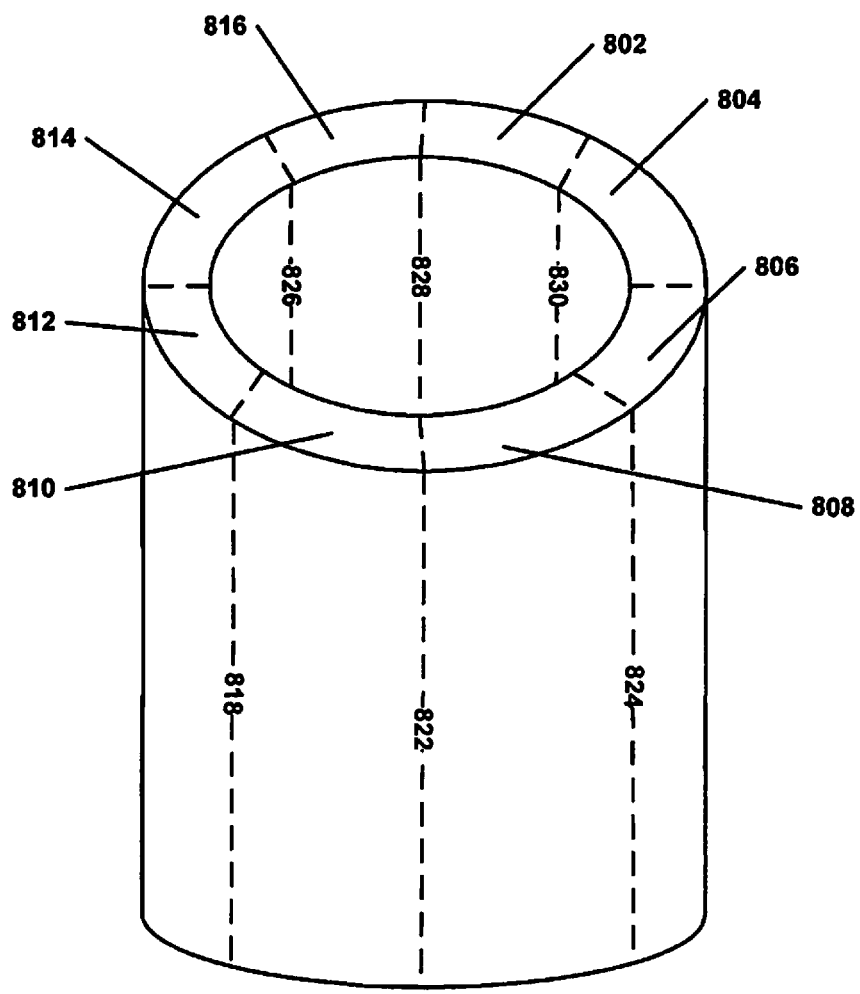
FIG. 8A illustrates a scored foreign body extractor end.

Referring now to FIG. 8A, yet another embodiment of the foreign object extractor is illustrated. As illustrated in FIG. 8A, the segmented end can initially be scored into a variable number of engagement segments 802, 804, 806, 808, 810, 812, 814, and 816. The number of segments illustrated is not meant as a limitation. The scored end can then be inserted into an orifice from which a foreign object is to be extracted. The scored end will then separate into segments along score lines 818, 822, 824, 826, 828, and 830 (note several score lines are not visible in this illustration) to engage the foreign body to be extracted. In this manner, segments will not become bent or otherwise pulled apart as they are being inserted and before they engage the foreign body. This embodiment as illustrated also comprises various end and internal adhesive coated surfaces, as described herein, to allow attachment to and extraction of foreign objects from the human body.

Figure 9:
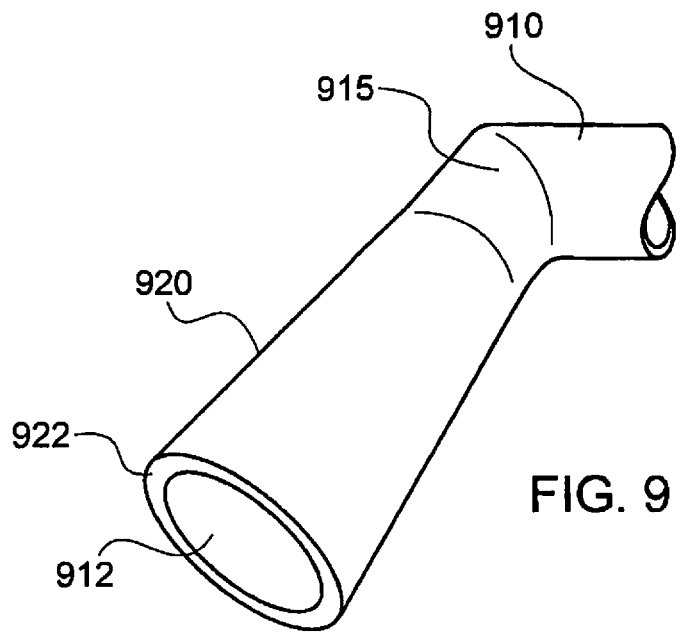
FIG. 9 illustrates a detail view of the flare end of an embodiment of the foreign object extractor that incorporates a fixed angle bend.

Referring to FIG. 9, a detail view of the engaging end of a fourth embodiment of the foreign object extractor that incorporates a fixed angle bend 915 is illustrated. The flared engaging end 920 is connected to the elongate body 910 with a fixed angle bend 915 so as to allow lumen 912 and annular adhesive coated surface 922 to reach around bends or corners. While illustrated as an approximate 45 degree angle, this is not meant as a limitation and the fixed angle bend can be manufactured to any suitable or desired angle between 10 and 90 degrees. The fixed angle bend 915 has utility with elongate bodies 910 that are rigid, resiliently (i.e., elastically) flexible or deformable, or plastically flexible or deformable.

Figure 10:
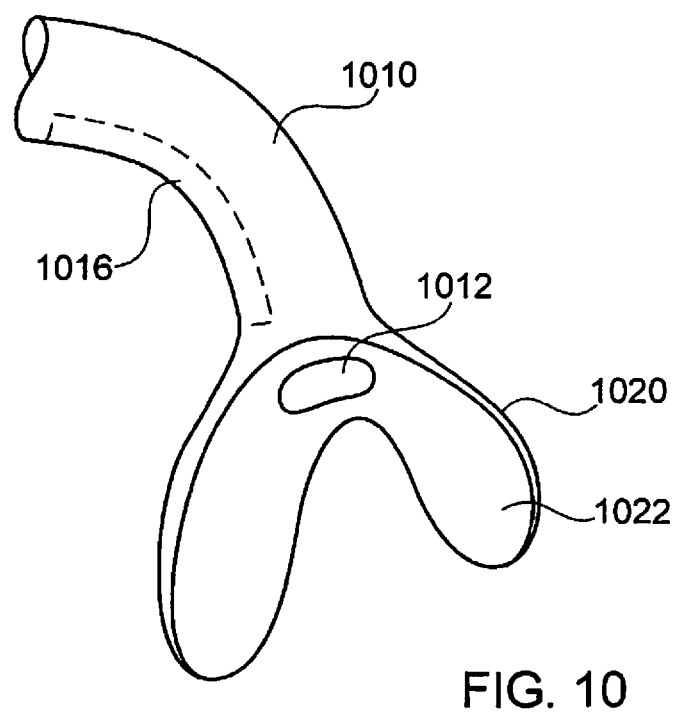
FIG. 10 illustrates a detail view of the engaging end of an embodiment of the foreign object extractor that incorporates a manually-bendable member and a pair of paddle-shaped adhesive grippers.

Referring to FIG. 10, a detail view of the engaging end of a fifth embodiment of the foreign object extractor that incorporates a manually-bendable member 1016 and a pair of paddle-shaped grippers 1020 is illustrated. The engaging end with paddle-shaped grippers 1020 is connected to the elongate body 1010, which includes a manually-bendable member 1016 adjacent to the gripper end so as to allow lumen 1012 and paddle-shaped adhesive coated surface 1022 to reach around bends or corners. The bendable member can be manually manipulated to any desired angle. The manually-bendable member 1016 has utility with elongate bodies 1010 that are rigid, resiliently (i.e., elastically) flexible or deformable, or plastically flexible or deformable (albeit not to such a degree as the manually-bendable member 1016). Furthermore, the manually-bendable member 1016 can alternately be incorporated on one or both of the paddle-shaped grippers 1020 in order to customize the shape of the gripping end to accommodate the foreign object and/or the body cavity.

While the manually-bendable member 1016 is illustrated as a thin strip of embedded metal, this is not meant as a limitation and the manually-bendable member can take other forms, including but not limited to embedded metal wires, adhesively-attached thin metal strips, adhesively-attached metal wires, and remotely-operated devices (e.g., cable actuators). Furthermore, although disclosed in combination, the manually-bendable member 1016 and paddle-shaped grippers 1020 need not be used in combination and can be used individually in other embodiments.

The transverse cross section of the engaging end of the extractor is nominally circular, although it may be embodied as oval or segmented (refer to the third and fifth embodiments described above). The extractor is made in various sizes to provide choice to the health care practitioner for addressing embedded foreign objects of various sizes and shapes. The size variations are provided by different flare angles for the engaging end (refer to FIGS. 4-6), and is also provided by a straightforward scaling up or down of the overall dimensions (i.e., different diameters).

The engaging end has a rapidly curing adhesive disposed on its outer rim or inner rim surfaces of the flared ends to form the adhesive coated surface. The adhesive is a quick curing type that is kept covered until time of use, at which time the protective cover is removed from the adhesive coated surface and the adhesive begins its curing process. This curing process may begin by uncovering the adhesive at which time curing begins and continues after coming in contact with the foreign object to be removed.

Figure 11:
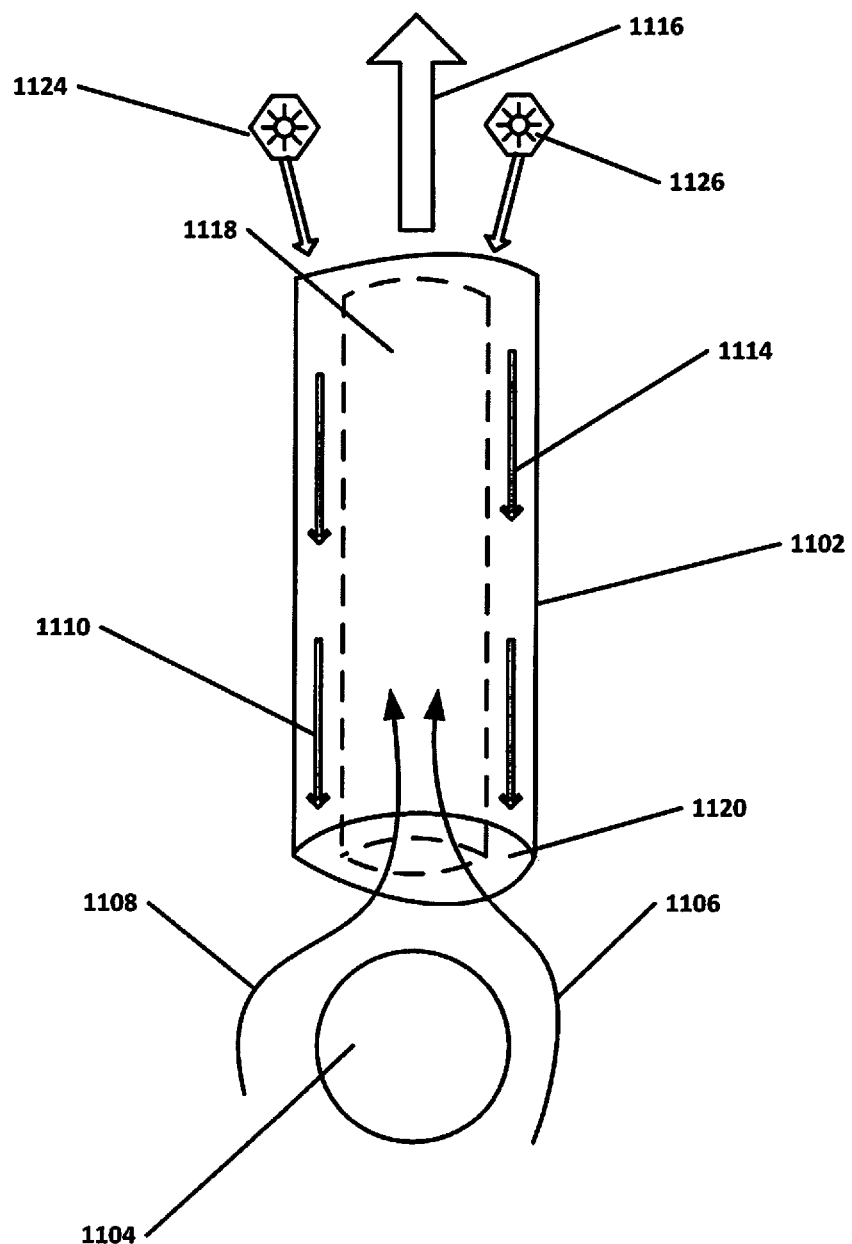
FIG. 11 illustrates a light curing adhesive embodiment.

Referring now to FIG. 11, an embodiment using light curing adhesive is illustrated. A suitable adhesive may also be the type of adhesive in which curing is facilitated by exposure to certain wavelengths of light (hereinafter "light curable adhesives"). Suitable light curing adhesives are illuminated with light in the visible or in the UV regions of the spectrum although this is not meant as a limitation. As light curing adhesives further are developed, other specific spectral regions for curing adhesives may also emerge which will be suitable for the functionality illustrated herein. In this embodiment tube 1102 is transparent and/or translucent and able to conduct light, further contains lumen 1118. When the tube is inserted into the patient, adhesive coated engaging end 1120, which is coated with a light curing adhesive, is brought into contact with the foreign body 1104. Illumination 1114, 1110 from an appropriate wavelength source 1124, 1126 is conducted through the walls of the tube 1102 to adhesive coated surface 1120 to effect curing in the same manner as would a fiber optic thread conduct light.

The engaging end of the extractor is brought into contact with the object to be removed and suction (illustrated by arrows 1106, 1108, and 1116), is applied through the central lumen of the extractor to forcefully urge the object into intimate contact with the adhesive coated engaging end surface 1120. This contact is maintained by continued application of vacuum pressure through the extractor until the adhesive has cured. Suction provides pressure for secure adhesion to the foreign object. When light curing adhesives are used, the combination of suction and appropriate spectral illumination 1114, 1110 will also result in the adhesive being cured to form the substantially permanent bond between the engaging end of the tube and the foreign object to be removed. Curing times for light curing adhesives are in the range of seconds, making such bonding useful for this application.

Once the bond is formed, the foreign object can then be removed from the living body by pulling on the extractor to which the foreign body has become adhered. Additionally to the adhesion, continued application of suction pressure through the extractor may be used to supplement connection of the extractor to the object.

To handle differing extraction situations, the extractor body (tube) may be semi-rigid and bendable or totally flexible. The body may be elastically flexible or plastically flexible. In an alternate embodiment, the extractor may be embodied having a rigid body—the rigidity being advantageous in some extraction situations. Materials such as polyolefins, aliphatic polycarbonates, Poly methyl methacrylate (PMMA) would all be suitable materials having light conducting properties for use as an extractor (tube) body.

While the foreign object extractor has been described in terms of use with a living body, it will be apparent to those skilled in the art that this same configuration can be used to extract foreign objects from inanimate objects as well, e.g., when small objects fall in cracks or other inaccessible location. Thus the disclosure herein should not be deemed to be limited to removal of objects from living bodies only.

A foreign object extractor for seizing hold of and extracting a foreign object from a living body has been described. It will be understood by those skilled in the art that the present invention may be embodied in other specific forms without departing from the scope of the invention disclosed and that the examples and embodiments described herein are in all respects illustrative and not restrictive. Those skilled in the art of the present invention will recognize that other embodiments using the concepts described herein are also possible. Further, any reference to claim elements in the singular, for example, using the articles "a," "an," or "the," is not to be construed as limiting the element to the singular.

What is claimed is:

1. An extractor for seizing and removing a foreign object from a natural orifice of the human body, the extractor comprising:
   a vacuum source, wherein the vacuum source is a vacuum bulb; and
   an elongate body having a lumen extending through the entire length of the elongate body, a first end of the elongate body being a flared engaging end and a second end of the elongate body opposite the first end being connected to the vacuum source so that the vacuum source is in fluid communication with the lumen and configured to draw suction through the flared engaging end, wherein the flared engaging end comprises paddle-shaped grippers having a quick-curing adhesive coated on the paddle-shaped grippers configured to contact the foreign object, and wherein each paddle-shaped gripper includes a manually-bendable member such that the paddle-shaped grippers can be bent to customize a shape of the flared engaging end before the flared engaging end is inserted into the natural orifice of the human body to remove the foreign object.

2. The extractor of claim 1, wherein the elongate body is resiliently flexible.

3. The extractor of claim 1, wherein at least a portion of the elongate body is plastically deformable.

4. The extractor of claim 1, wherein the elongate body is substantially rigid.

5. The extractor of claim 1, further comprising a removable cover disposed over the quick curing adhesive, the cover being removable prior to the extractor being used for seizing and removing the foreign object.

6. The extractor of claim 1 wherein the vacuum bulb comprises a textured surface.

7. A method for removing a foreign object from a natural orifice of the human body comprising:

bending, to a customized shape, paddle-shaped grippers of a flared distal end of an extractor tube having a lumen through the length of the tube and a proximal end, wherein each paddle-shaped gripper includes a manually-bendable member such that the paddle-shaped grippers can be bent to customize the shape of the flared distal end;

inserting the bent paddle-shaped grippers of the flared distal end into the natural orifice of the human body;

bringing an adhesive-coated end surface of the paddle shaped grippers of the distal end in contact with the foreign object lodged in the natural orifice of the human body;

applying a suction source to the proximal end of the tube using the suction source to draw suction through the adhesive-coated end surface of the paddle shaped grippers of the distal end to bring the foreign object in physical contact with the adhesive coated end surface of the paddle shaped grippers of the distal end, wherein the suction source is a vacuum bulb;

allowing the adhesive to cure to form a non-releasable bond between the end surface of the paddle shaped grippers of the distal end and the foreign object while the combined tube, adhesive coated end surface of the paddle shaped grippers of the distal end, and the foreign object remain in the natural orifice of the human body; and pulling the bonded extractor tube and foreign object from the natural orifice of the human body.

\* \* \* \* \*